US012714550B2

(12) United States Patent
Walsh et al.

(10) Patent No.: US 12,714,550 B2
(45) Date of Patent: Aug. 25, 2026

(54) MODIFIED TRABECULAR METAL SUTURE ANCHOR IMPLANT

(71) Applicant: Acumed LLC, Hillsboro, OR (US)

(72) Inventors: Joseph R. Walsh, Wentzville, MO (US); Tyler Krummenacher, St. Louis, MO (US)

(73) Assignee: Acumed LLC, Hillsboro, OR (US)

(*) Notice: Subject to any disclaimer, the term of this patent is extended or adjusted under 35 U.S.C. 154(b) by 0 days.

(21) Appl. No.: 19/081,809

(22) Filed: Mar. 17, 2025

(65) Prior Publication Data

US 2025/0387216 A1 Dec. 25, 2025

Related U.S. Application Data

(63) Continuation of application No. 17/625,251, filed as application No. PCT/US2020/041371 on Jul. 9, 2020, now Pat. No. 12,279,943.

(Continued)

(51) Int. Cl.

*A61B 17/04* (2006.01)
*A61F 2/00* (2006.01)
*A61F 2/08* (2006.01)

(52) U.S. Cl.

CPC ........ *A61F 2/0077* (2013.01); *A61B 17/0401* (2013.01); *A61B 2017/044* (2013.01);

(Continued)

(58) Field of Classification Search

CPC ... A61B 17/869; A61B 17/0401; A61B 17/56; A61B 2017/561; A61B 17/562;

(Continued)

(56) References Cited

U.S. PATENT DOCUMENTS

2010/0069958 A1* 3/2010 Sullivan ............. A61B 17/0642 606/232
2013/0035721 A1 2/2013 Brunelle (Continued)

FOREIGN PATENT DOCUMENTS

JP 2014-528750 A 10/2014
JP 2017-185238 A 10/2017

(Continued)

OTHER PUBLICATIONS

Extended European Search Report corresponding to related European Patent Application No. 20837319.1 mailed Oct. 9, 2023, 8 pages.

(Continued)

*Primary Examiner* — Samuel S Hanna
(74) *Attorney, Agent, or Firm* — Knobbe, Martens, Olson & Bear, LLP

(57) ABSTRACT

An anchor device for attaching suture material to bone includes a body portion having a first end and a second end. The body portion includes a trabecular mesh core that at least partially defines a central bore between the first end and the second end. The trabecular mesh core includes a plurality of openings configured to receive/allow/facilitate bone growth through the trabecular mesh core. The body portion also includes at least one thread extending spirally along an exterior of the trabecular mesh core. The anchor device further includes a post at least partially positioned within the central bore and rotatably coupled to the body portion, wherein the post comprises a fork extending from the second end of the body portion and configured to attach soft tissue to the bone using the suture material. The body portion and the post are additively manufactured from a biocompatible material.

17 Claims, 10 Drawing Sheets

Related U.S. Application Data

(60) Provisional application No. 62/979,676, filed on Feb. 21, 2020, provisional application No. 62/872,116, filed on Jul. 9, 2019.

(52) U.S. Cl.
CPC ................. *A61F 2002/0081* (2013.01); *A61F 2002/0817* (2013.01); *A61F 2002/0858* (2013.01)

(58) Field of Classification Search
CPC ........ A61B 2017/564; A61B 2017/567; A61B 2017/568; A61B 17/58; A61F 2/32; A61F 2/34; A61F 2/3662; A61F 2002/3611; A61F 2002/3625; A61F 2002/365
See application file for complete search history.

(56) References Cited

U.S. PATENT DOCUMENTS

| | | | |
|---|---|---|---|
| 2014/0194907 | A1 | 7/2014 | Bonutti et al. |
| 2015/0313586 | A1 | 11/2015 | Burkhart et al. |
| 2016/0166301 | A1 | 6/2016 | Papangelou et al. |
| 2017/0290656 | A1 | 10/2017 | Piccirillo et al. |
| 2018/0344463 | A1 | 12/2018 | Froster et al. |
| 2019/0076257 | A1 | 3/2019 | Dee et al. |
| 2019/0184058 | A1 | 6/2019 | Aihara et al. |
| 2019/0343564 | A1 | 11/2019 | Tempco et al. |
| 2019/0343565 | A1 | 11/2019 | Tempco et al. |
| 2020/0155137 | A1 | 5/2020 | Brunsvold et al. |
| 2022/0249220 | A1 | 8/2022 | Walsh et al. |

FOREIGN PATENT DOCUMENTS

| | | | |
|---|---|---|---|
| JP | 2017-538535 | A | 12/2017 |
| WO | 2021/007414 | A1 | 1/2021 |

OTHER PUBLICATIONS

Intention to grant, re European Application No. 20837319.1, dated Jan. 3, 2025.

International Preliminary Report on Patentability, re PCT Application No. PCT/US2020/041371, dated Jan. 20, 2022.

International Search Report and Written Opinion, re PCT Application No. PCT/US2020/041371, dated Oct. 7, 2020.

Office Action corresponding to related Japanese Patent Application No. 2022-500963 mailed Dec. 25, 2023, 11 pages.

* cited by examiner

MODIFIED TRABECULAR METAL SUTURE ANCHOR IMPLANT

CROSS REFERENCE TO RELATED APPLICATIONS

This application is continuation of U.S. patent application Ser. No. 17/625,251, filed Jan. 6, 2022, which is a U.S. National Phase of International Application No. PCT/US2020/041371, filed Jul. 9, 2020, which claims the benefit of U.S. Provisional Patent Application No. 62/872,116, filed on Jul. 9, 2019, and U.S. Provisional Patent Application No. 62/979,676 filed on Feb. 21, 2020, the contents of each of which are hereby incorporated herein by reference in their entireties. Any and all applications, if any, for which a foreign or domestic priority claim is identified in the Application Data Sheet of the present application are hereby incorporated by reference under 37 CFR 1.57.

FIELD OF THE DISCLOSURE

The field of the disclosure relates generally to suture anchors, and more specifically, to trabecular suture anchors formed by additive manufacturing, as well as modified versions thereof.

BACKGROUND OF THE DISCLOSURE

When soft tissue is disrupted from bone, surgical repair techniques are often implemented and necessary, including suturing damaged tissue to bone, to perform reconstructive surgery. Historically, the two damaged ends of a ligament or tendon were sutured together with hopes of providing lasting stability to an area and avoiding the development of arthritis and loss of overall use/functionality of a part of the body. Advancements in medicine improved this process by attaching suture to a bone anchor or by pushing suture or suture associated material (i.e., tendon graft, etc.) into a surgically created hole within a patient's bone via a bone anchor to stabilize an injury. The bone anchor is inserted into the hole pushing the suture/suture associated materials into the hole in an attempt to stabilize the injury and serve as a "cap" to prevent the suture/suture associated materials from backing out of the hole and destabilizing the injury again. The bone anchor allows the surgeon to connect tissue to bone using suture or suture associated materials. At least some known suture anchors are attached to the bone by screwing the anchors into a hole formed in the bone. However, it is known that some current anchors back out of the bone over time or may decouple from the bone under trauma.

Furthermore, at least some known anchors are formed from plastics, such as PEEK, and are subject to breakage and decoupling. Such plastic anchors are solid-bodied and do not integrate with the bone, which may lead to decoupling. Moreover, at least some known plastic anchors are manufactured by machining, and as such, cannot be machined to as small as a size as may be required. Additionally, plastics have a higher risk of biocomposite reaction in some patients, which may require the anchor to be removed surgically. At least some known anchors include multiple pieces and require assembly prior to use, which may increase manufacturing time and costs.

BRIEF DESCRIPTION OF THE DISCLOSURE

In one embodiment, an anchor device for attaching suture material and/or tissue allograft/autograft to bone is provided. The anchor device includes a body portion having a first end and a second end. The body portion includes a trabecular mesh core that at least partially defines a central bore between the first end and the second end. The body portion also includes at least one thread extending spirally along an exterior of the trabecular mesh core between the first end and the second end. The anchor device further includes a post at least partially positioned within the central bore and rotatably coupled to the body portion, wherein the post comprises a fork extending from the second end of the body portion and configured to attach soft tissue to the bone using the suture material.

In another embodiment, an anchor device for attaching suture material to bone is provided. The anchor device includes a body portion having a first end and a second end. The body portion includes a trabecular mesh core that at least partially defines a central bore between the first end and the second end. The trabecular mesh core includes a plurality of openings configured to facilitate bone growth through the trabecular mesh core. The anchor device also includes a post at least partially positioned within the central bore and rotatably coupled to the body portion. The post includes a fork extending from the second end of the body portion and configured to attach soft tissue to the bone using the suture material. The body portion and the post are additively manufactured from a biocompatible material.

DETAILED DESCRIPTION OF THE DISCLOSURE

Figure 1:
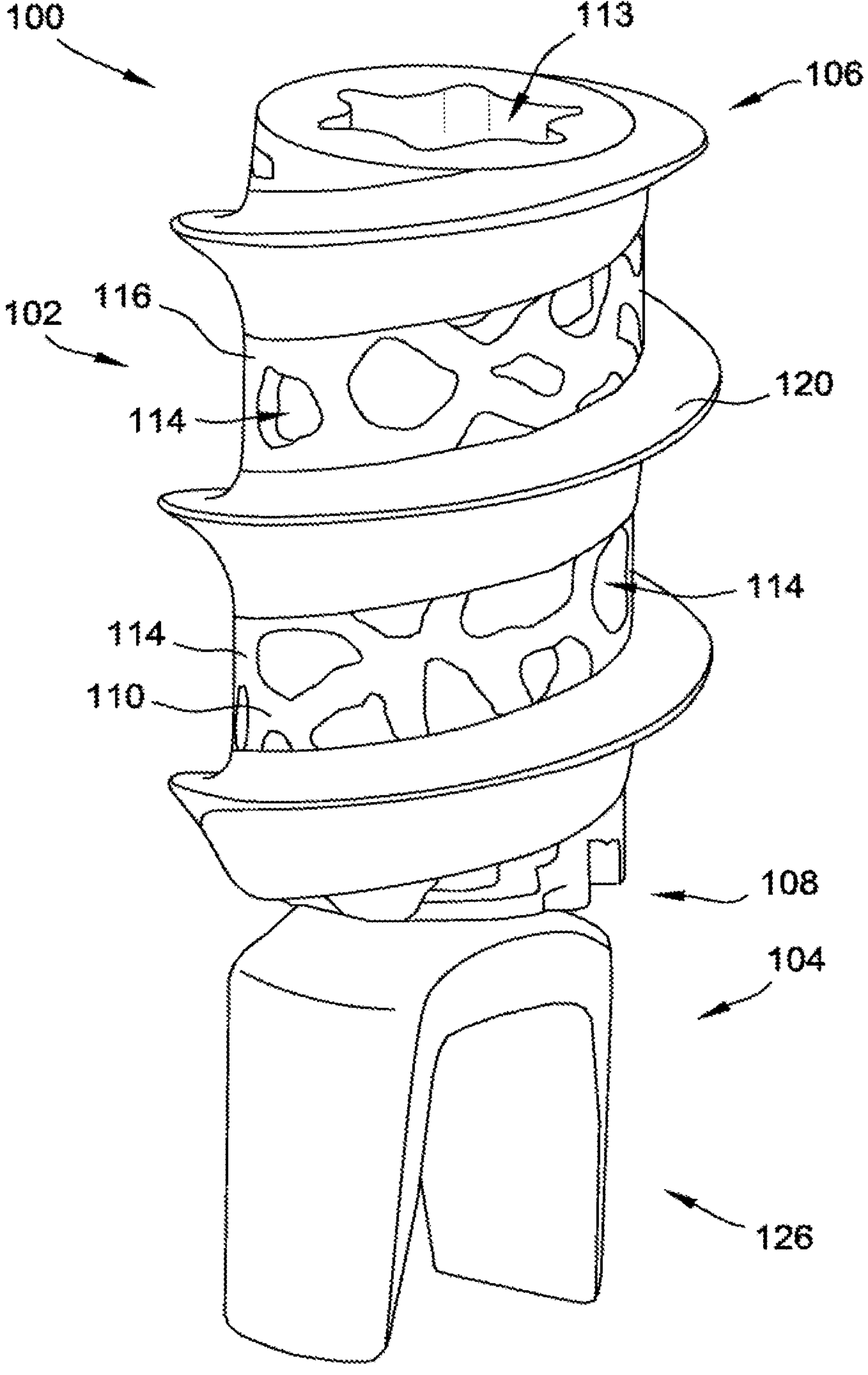
FIG. 1 is a perspective view of a first embodiment of a trabecular suture anchor.
Figure 2:
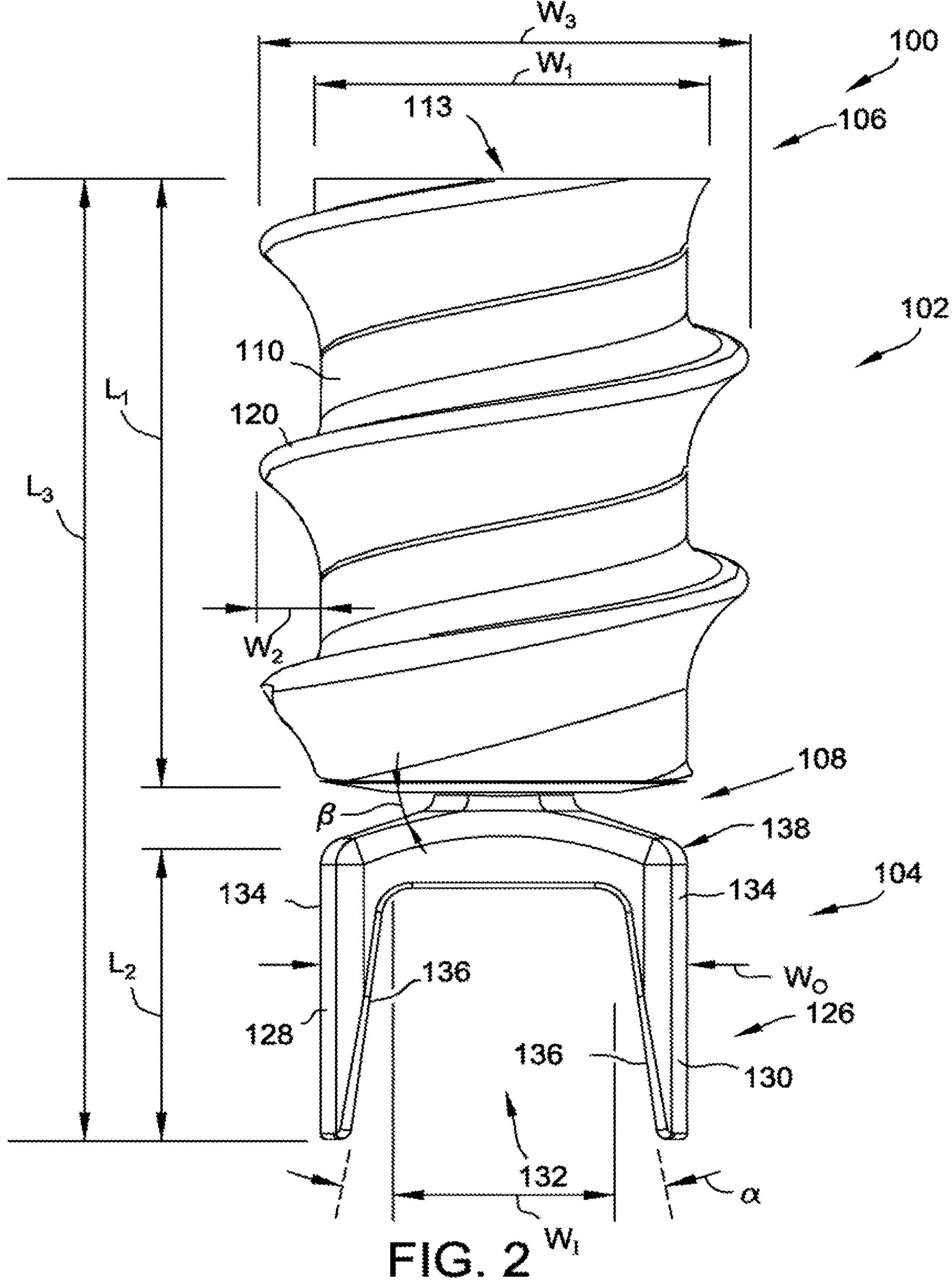
FIG. 2 is a front view of the trabecular suture anchor shown in FIG. 1.
Figure 3:
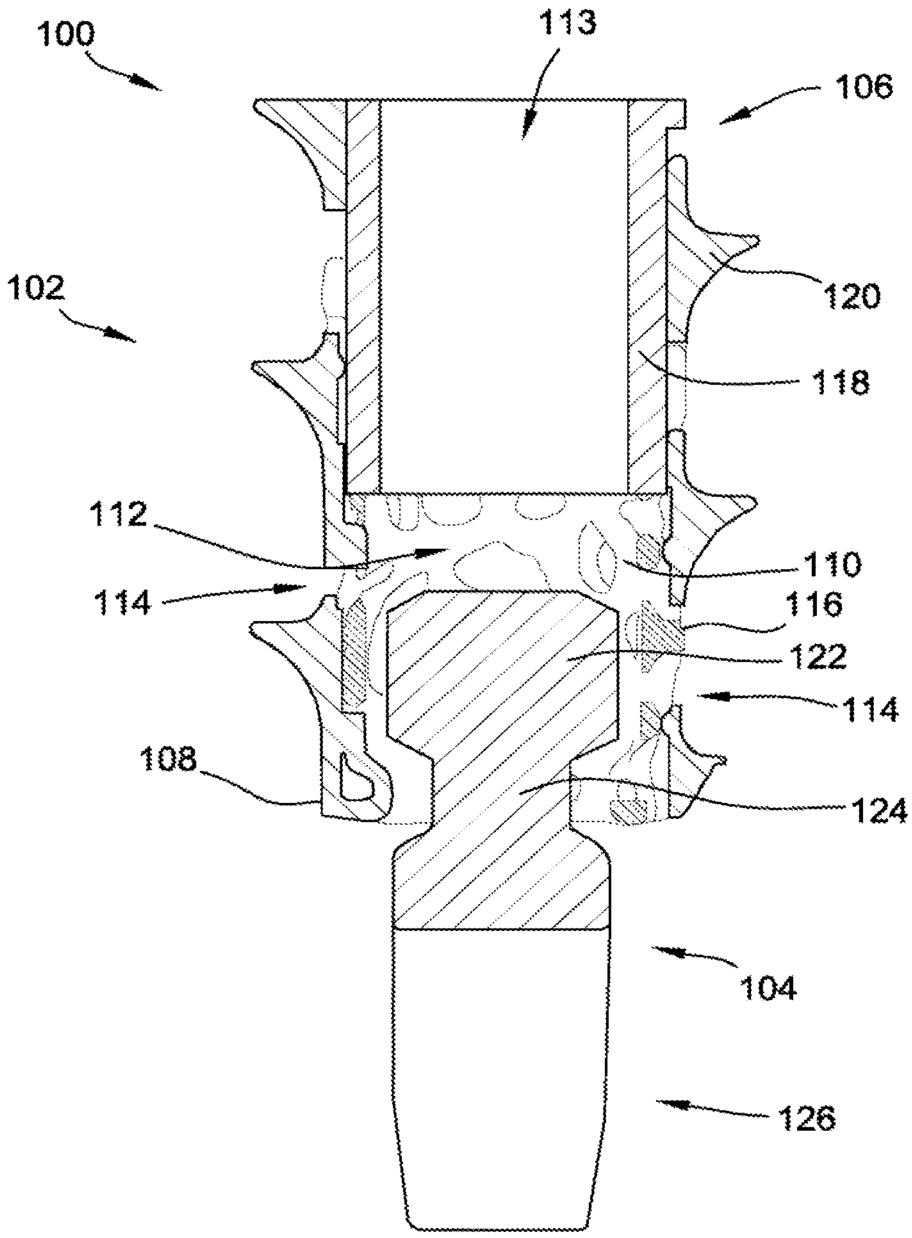
FIG. 3 is a cross-sectional view of the trabecular suture anchor shown in FIG. 1.

FIG. 1 is a perspective view of a first embodiment of a trabecular suture anchor device 100. FIG. 2 is a front view of trabecular suture anchor device 100. FIG. 3 is a cross-sectional view of trabecular suture anchor device 100. In the exemplary embodiment, anchor device 100 includes a body portion 102 and a post 104. Body portion 102 includes a first end 106 and an opposing second end 108 and is made up of a trabecular mesh core 110 that extends from first end 106 to second end 108. Mesh core 110 defines a central bore 112 that extends through body portion 102 from first end 106 to second end 108. Furthermore, body portion 102 includes an opening 113 at first end 106 configured to receive a driver tool therein. In the exemplary embodiment, opening 113 is a Torx (hexalobe) shaped opening. It should be understood that opening 113 can assume other shapes, such as crosses or squares, to conform to a variety of drives for screwing anchor device 100 into and out of the bone. More specifically, the shape of opening 113 may be based on the size of anchor device 100, with smaller anchor devices 100 having the illustrated hexalobe shape. Furthermore, the hexalobe shape increases the surface area of anchor device 100 in contact with the driver tool and, as such, reduces the risk of stripping opening 113.

In the exemplary embodiment, mesh core 110 also includes a plurality of openings 114 that extend from central bore 112 to an exterior 116 of mesh core 110. When implanted into bone, openings 114 allow the surrounding bone to grow into and through mesh core 110 to firmly secure anchor device 100 to the bone. In the exemplary embodiment, mesh core 110 includes at least one of a triply periodic minimal surface (TPMS), orthofoam lattice, and voronoi lattice. Generally, mesh core 110 includes any style mesh that facilitates operation as described herein.

Additionally, in the exemplary embodiment, mesh core 110 includes a 0.20 millimeter (mm) strut target and a 0.40 mm pore target. That is, openings 114 are sized at approximately 0.40 mm and the mesh material itself that defines openings 114 is made up of a plurality of struts that are sized at approximately 0.15 to approximately 0.20 mm. More specifically, openings 114 may be made up of a combination of a plurality of pore openings having a size of about 0.15 mm and a plurality of channel openings having a length of about 0.40 mm. As used herein, the term "pore opening" is used to describe a small opening 114 when viewed normal to the external cylinder of mesh core 110. Generally, openings 114 and the struts may be any size that facilitates operation of anchor device 100 as described herein. In the exemplary embodiment, mesh core 110 also includes a roughness magnitude of approximate 0.175 mm and a roughness frequency or approximately 2500. As used herein, "roughness magnitude" is used describe the average height of the roughness features (peaks and valleys) that make up mesh core 110, and "roughness frequency" is used to describe the number of peaks/valleys of the roughness features in a 1.0 cubic sample of mesh core 110.

Anchor device 100 provides an important technical advantage by providing a means of osteointegration/bone ingrowth throughout the body portion of anchor device 100 while in bone. The mesh/porosity of mesh core 110 allows bone to integrate circumferentially through the 3D trabecular mesh body of anchor device 100. After anchor device 100 is implanted, the patient's bone will begin to grow into and through trabecular mesh of mesh core 110, thus anchoring it into the bone. When bone is fully integrated/fused to itself through mesh core 110, anchor device 100 will substantially increase overall strength and greatly reduce or eliminate disengagement of anchor device 100 from the bone.

As best shown in FIG. 3, body portion 102 also includes a solid-bodied inner wall 118 extending from first end 106 and at least partially defining central bore 112. Inner wall 118 extends only a partial distance along the length of body portion 102 toward second end 108. For example, inner wall 118 may extend approximately halfway between first end 106 and second end 108. In the exemplary embodiment, inner wall 118 extends along mesh core 110 such that mesh core 110 circumscribes inner wall 118.

Body portion 102 also includes at least one thread 120 extending spirally along exterior 116 of mesh core 110 between first end 106 and second end 108. While mesh core 110 is trabecular with openings 114, threads 120 are solid-bodied and do not contain any openings or cavities. Solid-bodied threads 120 facilitate better engagement with bone material to retain anchor device 100 within the bone.

Still referring to FIG. 3, post 104 includes a head 122, a shank 124 extending from head 122, and a fork 126 extending from shank 124. In the exemplary embodiment, head 122 is positioned within central bore 112 and includes an outer diameter D1 that is greater than an inner diameter D2 at second end 108 of body portion 102 to retain head 122 within central bore 112. Post 104 is rotatably coupled to body portion 102 such that post 104 is able to rotate freely with respect to body portion 102. As described in further detail herein, fork 126 is configured to attach soft tissue to the bone using suture, allographic, autographic, and other suture associated material(s) (i.e., tendon graft, etc.).

In the exemplary embodiment, anchor device 100 is additively manufactured from a biocompatible material. Specifically, anchor device 100 is additively manufactured from a biocompatible metallic material. More specifically, anchor device 100 is additively manufactured from titanium, such as, but not limited to Grade 23 Titanium. As such, body portion 102 and post 104 are additively manufactured together such that no assembly is required post manufacturing. Furthermore, additive manufacturing allows mesh core 110 and threads 120 to be formed simultaneously during manufacturing.

As described herein, additively manufacturing mesh core 110 with openings 114 allows for bone to grow into and through anchor device 100, which will inevitably strengthen the surgical site by lessening the potential for the anchor to dislodge or back out. Furthermore, anchor device 100 provides an advantage over conventional bone anchors as the titanium structure strengths the implants itself, as opposed to PEEK options that may break during insertion. Another advantage is that the titanium is osteophilic as opposed to the osteophobic properties of PEEK.

The simultaneous manufacturing of body portion 102 and post 104 attached fork/saddle is also advantageous compared to other market options as a surgeon will not have to be concerned that an independently manufacture fork will separate from the anchor body prior to implantation as anchor device 100 has an all-in-one piece design. Anchor device 100 also allows a surgeon to attach a needle and/or suture to the suture/graft prior to inserting anchor device 100. This option provides a potential patient safety advantage because the surgeon does not have to attach a needle to the suture after anchor device 100 is screwed into the bone, thereby avoiding any disruptions or unintentional damage of a patient's bone or soft tissues.

Referring now to FIG. 2, body portion 102 and mesh core 110 include a first width W1 of approximately 2.50 millimeters (mm) to approximately 3.0 mm. As used herein, the term "approximately" is used to describe a tolerance range and includes measurements within 0.1 mm of the included range. Threads 120 include a second width W2 of approximately 0.50 mm to approximately 0.075 mm. As such, anchor device 100 includes a total width W3 of approximately 3.5 mm to approximately 4.5 mm.

Similarly, in exemplary embodiment, body portion 102 includes a first length L1 of approximately 5.5 mm. Fork 126 includes a second length L2 of approximately 2.60 mm to approximately 2.90 mm. Anchor device 100 includes an overall third length L3 of approximately 8.50 mm to approximately 8.70 mm.

Still referring to FIG. 2, fork 126 includes a first prong 128 and a second prong 130 that is spaced from first prong 128. More specifically, fork 126 defines a suture trough or gap 132 between prongs 128 and 130 that is configured as a trough to receive suture material therein. In the exemplary embodiment, fork 126 defines an outer width Wo taken between opposing exterior surfaces 134 of prongs 128 and 130 of approximately 2.50 mm. Each prong 128 and 130 also includes an obliquely oriented inner surface 136 such that each prong 128 and 130 tapers in width in a distal direction. More specifically, opposing inner surfaces 136 define an angle $\alpha$ of approximately 13.5 degrees and approximately 14.5 degrees. Furthermore, fork 126 defines an inner width Wi taken between opposing inner surfaces 136 at a proximal end of prongs 128 and 130 of approximately 1.40 mm to approximately 2.00 mm. The suture and suture associated materials are manually passed through prongs 128 and 130 of fork 126 and can be secured to the driver tool to pull taut, thereby seating the suture in the suture trough 132 and securing anchor device 100 to the driver tool (not pictured). The suture and suture associated materials can pass through the suture trough 132 either with or without a needle attached, depending on the need of the specific operation. Additionally, fork 126 provides the means for easily loading suture/suture associated material onto the distal aspect of anchor device without requiring a special suture threading tool.

In the exemplary embodiment, fork 126 includes a shoulder 138 at the proximate end of each prong 128 and 130. Shoulders 138 are obliquely oriented with respect to second end 108 of body portion 102 such that shoulders 138 form an angle $\beta$ of approximately 40 degrees with respect to second end 108 to reduce friction of fork 126 rotation. Furthermore, shoulders 138 are rounded to include a radius of approximately 0.25 mm.

Figure 4:
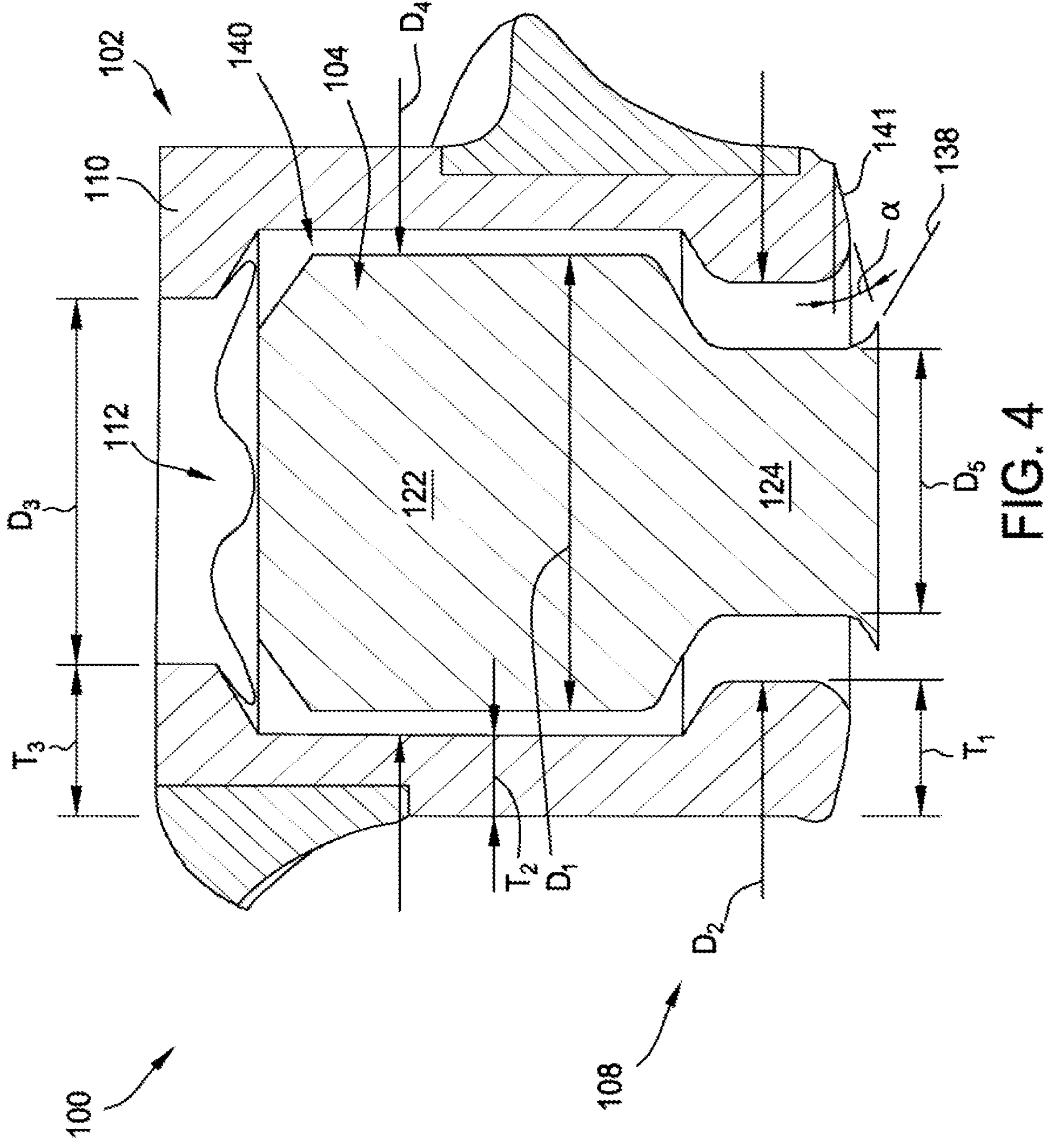
FIG. 4 is an enlarged view of a portion of the trabecular suture anchor shown in FIG. 1 illustrating the interaction between a body of the anchor and a post of the anchor.

FIG. 4 is an enlarged view of a portion of anchor device 100 illustrating the interaction between body portion 102 and post 104. More specifically, FIG. 4 illustrates head 122 positioned within a cavity 140 of central bore 112. In the exemplary embodiment, mesh core 110 includes a first thickness T1 at second end 108 and a second thickness T2 immediately proximal of second end 108. Furthermore, mesh core 110 includes a third thickness T3 immediately proximal of the section of mesh core 110 with second thickness T2. In the exemplary embodiment, second thickness T2 is less than first thickness T1 and third thickness T3 such that central bore 112 defines cavity 140 to contain head 122. In one embodiment, third thickness T3 is greater than first thickness T1. Alternatively, third thickness T3 is substantially similar to first thickness T1.

In the exemplary embodiment, second end 108 mesh core 110, having first thickness T1, defines a diameter D2 of central bore 112 that is less than a diameter D1 of head 122 of post 104. Similarly, the portion of mesh core 110 having third thickness T3 defines a diameter D3 of central bore that is smaller than diameter D2 of head 122. As such, head 122 is restrained within cavity 140 and cannot be removed from body portion 102 through second end 108. In an alternative embodiment, mesh core 110 includes only first thickness T1 and second thickness T2, and shoulders 138 of fork 126 contact second end 108 of body portion 102 to prevent excess axial movement of post 104 within central bore 112. More specifically, in one embodiment, a distal surface 141 of second end 108 is oriented at an angle $\sigma$ of approximately 10 degrees to separate body portion 102 from fork 126 to reduce friction of fork 126 rotation.

As shown in FIG. 4, cavity 140 includes a diameter D4 that is larger than diameter D1 of head 122 and diameter D2 of second end 108 is larger than a diameter D5 of shank 124. Additionally, the axial length of cavity 140 is larger than the axial length of head 122. As such, head 122 and shank 124 are able to not only rotate freely in central bore 112, but also allowed restricted axial movement and may be obliquely oriented with respect to body portion 102. The ability to be angled with respect to body portion 102 enables anchor device 100 to be secured to the patient's bone at various angles and does not require post 104 to be parallel in orientation with body portion 102. The cylindrical body portion 102 coupled with the built-in clearance (within second end 108 of mesh core 110) that head 122 and shank 124 reside within allows for a 360 degrees unabated rotation of fork 126 respective to the body portion 102.

Figure 5:
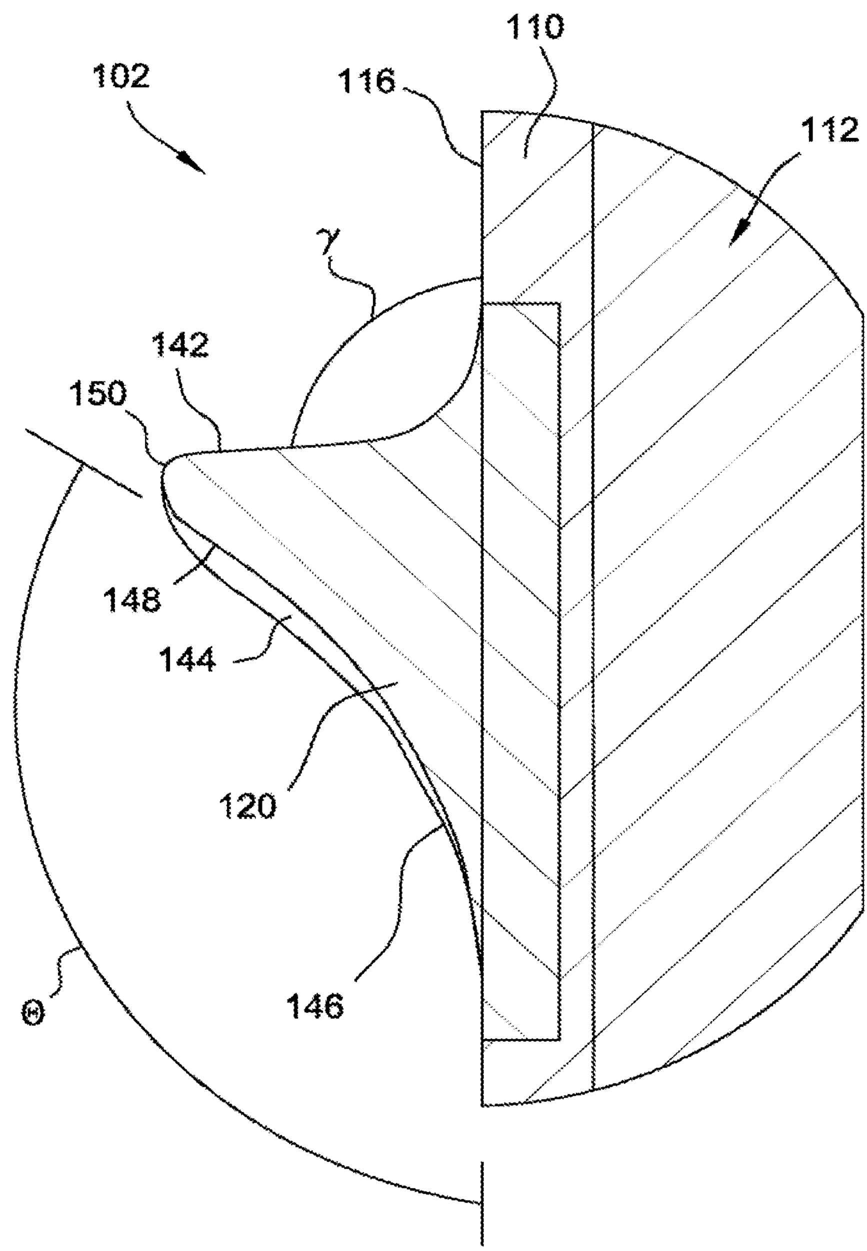
FIG. 5 is an enlarged view of a portion of the trabecular suture anchor shown in FIG. 1 illustrating exemplary threading on a body of the anchor.

FIG. 5 is an enlarged view of body portion 102 illustrating a detailed view of thread 120. In the exemplary embodiment, thread 120 includes a top surface 142 that is oriented at an angle $\gamma$ of approximately 93 degrees with respect to exterior surface 116 of mesh core 110 above thread 120. Thread 120 also includes a bottom surface 144 that includes a curved portion 146 extending from exterior surface 116 and a planar portion 148 extending from curved portion 146. In the exemplary embodiment, curved portion 146 defines a radius of approximately 0.8 mm, and planar portion 148 is oriented at an angle $\theta$ of approximately 125 degrees with respect to exterior surface 116 below thread 120. Furthermore, thread 120 includes an edge 150 that is rounded at a radius of approximately 0.05 mm.

In operation, the suture and suture associated materials are manually passed through prongs 128 and 130 of fork 126 and can be secured to the driver tool to pull taut, thereby seating the suture in the suture trough 132 and securing anchor device 100 to the driver tool (not pictured). The drive tool is then inserted into opening 113 and contacts head 122 of post 104 to push suture and/or suture associated materials into a pre-made hole in the patient's bone by fork 126. The drive tool can then rotate to screw anchor device 100 and suture/suture associated materials into the bone. The suture and/or suture associated materials are then adhered/anchored to other tissues as per practitioner preference by stretching the suture/suture associated materials to a separately created hole in the same manner described above. The suture or suture associated materials exit on any side of anchor device 100 post implantation into the bone. Bone ingrowth/osteointegration through mesh core 110 during the healing process further stabilizes anchor device 100 into the bone.

This surgically implanted anchor provides an important technical advantage by providing a means of osteointegration/bone ingrowth throughout the core/body of the implant while in bone. The mesh/porosity of the anchor allows bone to integrate circumferentially through the 3D trabecular mesh body of the implant.

Another advantage is that this implant does not require any threading of suture as it does not contain any eyelet throughout the construct. Furthermore, the 360 degree rotating fork can be stabilized from its dynamic state simply by holding the suture within the tines of the fork with manual tension giving a surgeon control of the entire implant throughout the implantation process.

The design of this implant provides a clinical advantage by eliminating or greatly reducing mechanical failure of the anchor due to the osteointegration thus eliminating or greatly reducing hardware disengagement.

In summary, the present embodiment describes 3D-Printed Osteointegrating Trabecular Metal Bone Anchors with affixed fork suture trough for use in attaching tissue to bone. The anchor includes a solid threaded bone anchor around a trabecular mesh core body having a major diameter, a minor diameter, a drive head, and a distally located freely articulating fork. A suture trough is formed between the tines of the fork having a width greater than or equal to the diameter of the suture and suture associated materials and a depth below the minor diameter greater than or equal to the diameter of the suture and suture associated materials. The suture seats within the suture trough of the fork during insertion of the bone anchor into the bone. The present embodiment allows needles to be attached to the suture and suture associated materials prior to insertion of the bone anchor into the bone, allows for osteointegration/bone ingrowth lessening the potential for the implant to dislodge, and an all-in-one piece design eliminating a surgeon concerns that a separate fork will separate from the anchor driver prior to implantation.

Figure 6:
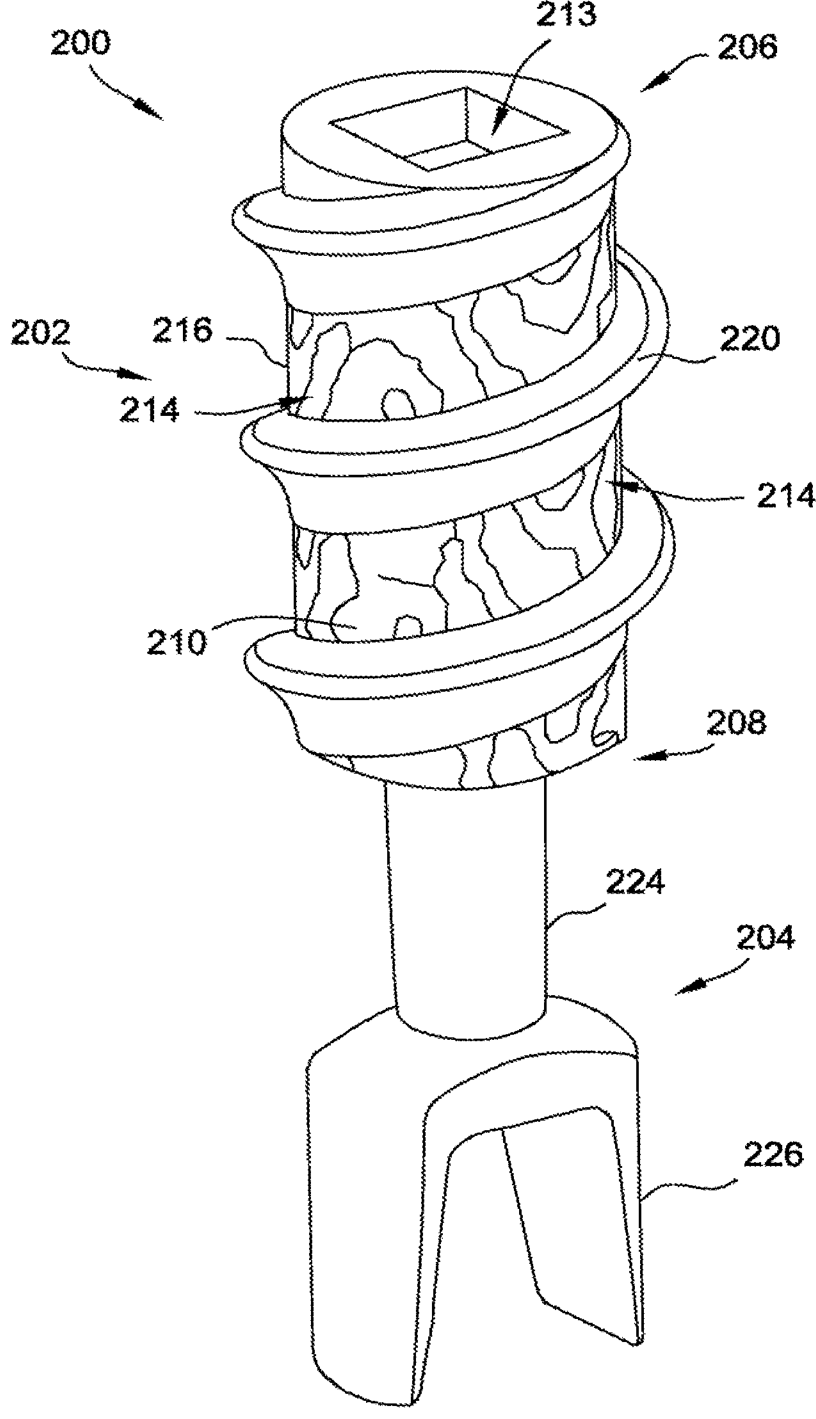
FIG. 6 is a perspective view of a second embodiment of a trabecular suture anchor.
Figure 7:
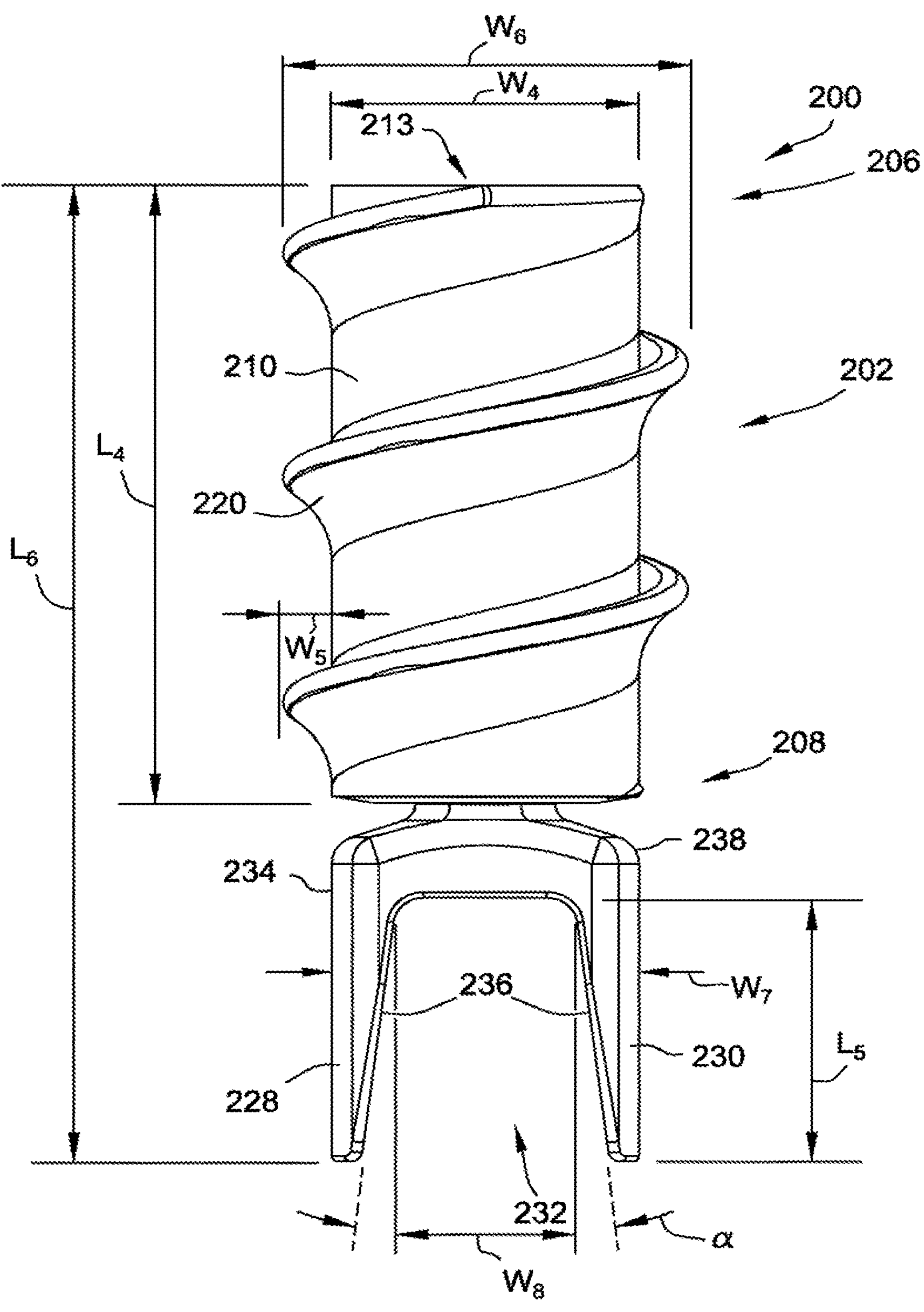
FIG. 7 is a front view of the trabecular suture anchor shown in FIG. 6.
Figure 8:
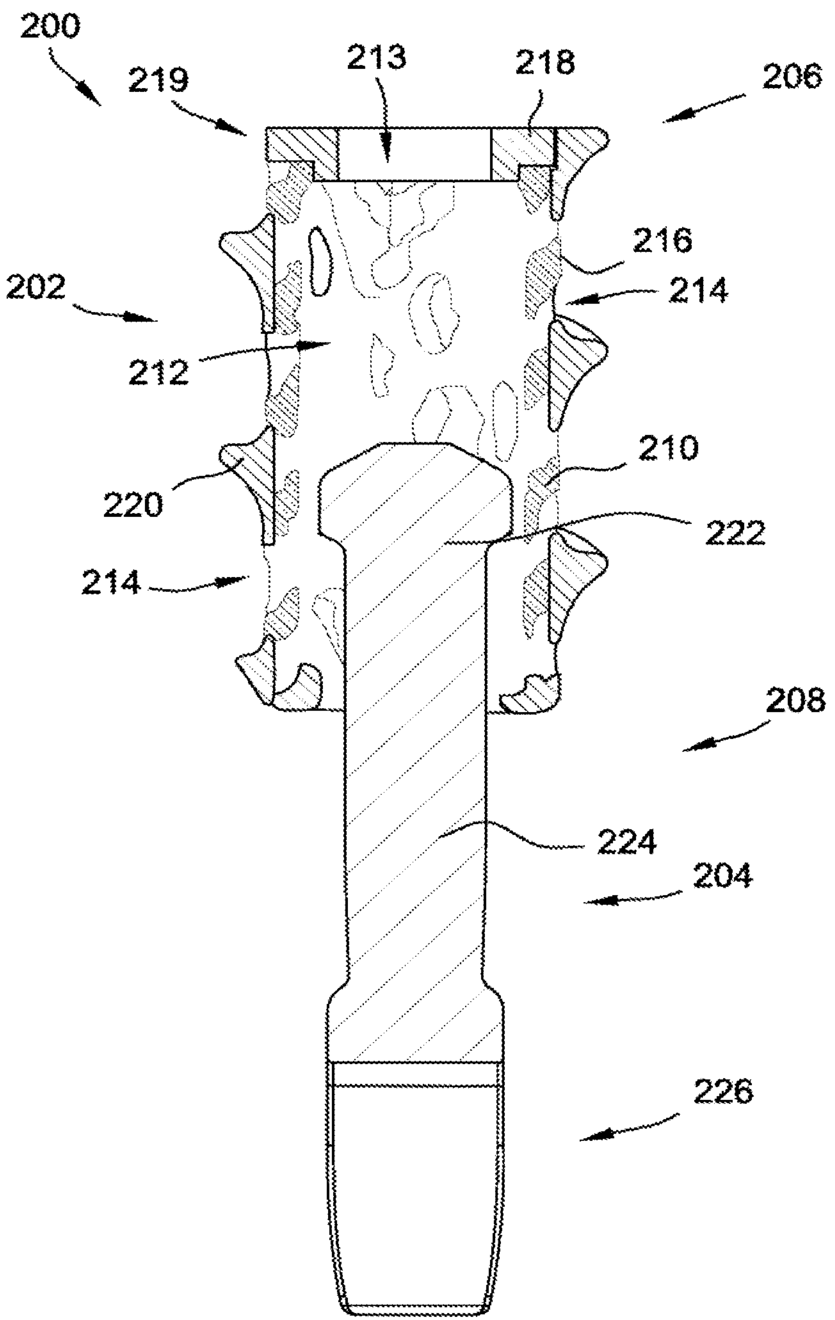
FIG. 8 is a cross-sectional view of the trabecular suture anchor shown in FIG. 6.
Figure 9:
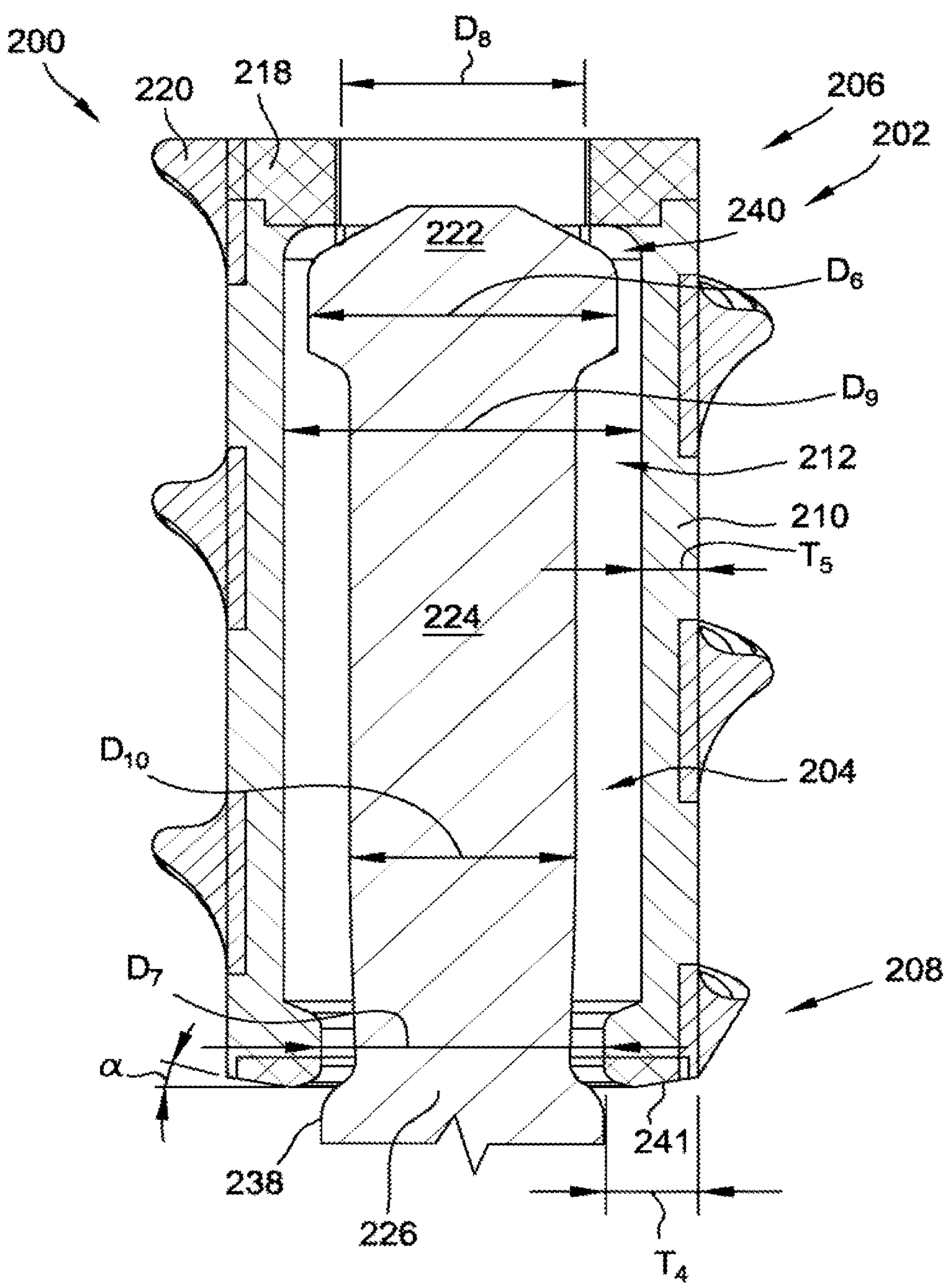
FIG. 9 is an enlarged view of a portion of the trabecular suture anchor shown in FIG. 6 illustrating the interaction between a body of the anchor and a post of the anchor.

FIG. 6 is a perspective view of a trabecular suture anchor device 200. FIG. 7 is a front view of trabecular suture anchor device 200. FIG. 8 is a cross-sectional view of trabecular suture anchor device 200. FIG. 9 is an enlarged view of a portion of anchor device 200 illustrating the interaction between a body of the anchor and a post of the anchor. In the exemplary embodiment, anchor 200 includes a body portion 202 and a post 204. Body portion 202 includes a first end 206 and an opposing second end 208 and is made up of a trabecular mesh core 210 that extends from first end 206 to second end 208. Mesh core 210 defines a central bore 212 that extends through body portion 202 from first end 206 to second end 208. Furthermore, body portion 202 includes an opening 213 at first end 206 configured to receive a driver tool therein. In the exemplary embodiment, opening 213 is a square-shaped opening. It should be understood that opening 213 can assume other shapes, such as a cross or a hexalobe, to conform to a variety of drives for screwing anchor device 200 into and out of the bone. More specifically, the shape of opening 213 may be based on the size of anchor device 200.

In the exemplary embodiment, mesh core 210 also includes a plurality of openings 214 that extend from central bore 212 to an exterior 216 of mesh core 210. When implanted into bone, openings 214 allow the surrounding bone to grow into and through mesh core 210 to firmly secure anchor device 200 to the bone. In the exemplary embodiment, mesh core 210 includes at least one of a triply periodic minimal surface (TPMS), orthofoam lattice, and voronoi lattice. Generally, mesh core 210 includes any style mesh that facilitates operation as described herein.

Additionally, in the exemplary embodiment, mesh core 210 includes a 0.20 millimeter (mm) strut target and a 0.40 mm pore target. That is, openings 214 are sized at approximately 0.40 mm and the mesh material itself that defines openings 214 is made up or a plurality of struts that are sized at approximately 0.15 to approximately 0.20 mm. More specifically, openings 214 may be made up of a combination of a plurality of pore openings having a size of about 0.15 mm and a plurality of channel openings having a length of about 0.40 mm. As used herein, the term "pore opening" is used to describe a small opening 214 when viewed normal to the external cylinder of mesh core 210. Generally, openings 214 and the struts may be any size that facilitates operation of anchor device 200 as described herein. In the exemplary embodiment, mesh core 210 also includes a roughness magnitude of approximate 0.175 mm and a roughness frequency or approximately 2500. As used herein, "roughness magnitude" is used describe the average height of the roughness features (peaks and valleys) that make up mesh core 210, and "roughness frequency" is used to describe the number of peaks/valleys of the roughness features in a 1.0 cubic sample of mesh core 210.

Anchor device 200 provides an important technical advantage by providing a means of osteointegration or bone ingrowth throughout the body portion of anchor device 200 while in bone. The porosity of mesh core 210 allows bone to integrate circumferentially through the 3D trabecular mesh body of anchor device 200. After anchor device 200 is implanted, the patient's bone will begin to grow into and through trabecular mesh of mesh core 210, thus anchoring it into the bone. When bone is fully integrated/fused to itself through mesh core 210, anchor device 200 will substantially increase overall strength and greatly reduce or eliminate disengagement of anchor device 200 from the bone.

As best shown in FIG. 8, body portion 202 also includes a solid-bodied inner ring 218 extending from first end 206 and at least partially defining central bore 212. Inner ring 218 extends only a partial length of body portion 202 toward second end 208. For example, inner ring 218 may extend a length of approximately 0.5 mm. In the exemplary embodiment, inner ring 218 extends radially a complete thickness of body portion 102 from central bore 212 to an exterior surface 219 of inner ring 218 that is substantially flush with exterior surface 216 of mesh core 210.

Body portion 202 also includes at least one thread 220 extending spirally along exterior 216 of mesh core 210 between first end 206 and second end 208. In the exemplary embodiment, threads 220 may also extend along exterior surface 219 of ring 218 at first end 206. While mesh core 210 is trabecular with openings 214, threads 220 are solid-bodied and do not contain any openings or cavities. Solid-bodied threads 220 facilitate better engagement with bone material to retain anchor device 200 within the bone.

Referring to FIGS. 8 and 9, post 104 includes a head 222, a shank 224 extending from head 222, and a fork 226 extending from shank 224. In the exemplary embodiment, head 222 is positioned within central bore 212 and includes an outer diameter D6 that is greater than an inner diameter D7 at second end 208 of body portion 202 to retain head 222 within central bore 212. Post 204 is rotatably coupled to body portion 202 such that post 204 is able to rotate freely with respect to body portion 202. As described in further detail herein, fork 226 is configured to attach soft tissue to the bone using suture, allographic, autographic, and other suture associated material(s) (i.e., tendon graft, etc.).

In the exemplary embodiment, anchor device 200 is additively manufactured from a biocompatible material. Specifically, anchor device 200 is additively manufactured from a biocompatible metallic material. More specifically, anchor device 200 is additively manufactured from titanium. As such, body portion 202 and post 204 are additively manufactured together such that no assembly is required post manufacturing. Furthermore, additive manufacturing allows mesh core 210 and threads 220 to be formed simultaneously during manufacturing.

As described herein, additively manufacturing mesh core 210 with openings 214 allows for bone to grow into and through anchor device 200, which will inevitably strengthen the surgical site by lessening the potential for the anchor to dislodge or back out. Furthermore, anchor device 200 provides an advantage over conventional bone anchors as the titanium structure strengths the implants itself, as opposed to PEEK options that may break during insertion. Another advantage is that the titanium is osteophilic as opposed to the osteophobic properties of PEEK.

The simultaneous manufacturing of body portion 202 and post 204 attached fork/saddle is also advantageous compared to other market options as a surgeon will not have to be concerned that an independently manufactured fork will separate from the anchor body prior to implantation as anchor device 200 has an all-in-one piece design. Anchor device 200 also allows a surgeon to attach a needle and/or suture to the suture/graft prior to inserting anchor device 200. This option provides a potential patient safety advantage because the surgeon does not have to attach a needle to the suture after anchor device 200 is screwed into the bone, thereby avoiding any disruptions or unintentional damage of a patient's bone or soft tissues.

Referring now to FIG. 7, body portion 202 and mesh core 210 include a width W4 of approximately 2.50 millimeters (mm) to approximately 3.0 mm. As used herein, the term "approximately" is used to describe a tolerance range and includes measurements within 0.1 mm of the included range. Threads 220 include a width W5 of approximately 0.50 mm to approximately 0.075 mm. As such, anchor device 200 includes a total width W6 of approximately 3.5 mm to approximately 4.5 mm.

Similarly, in exemplary embodiment, body portion 202 includes a length L4 of approximately 5.5 mm. Prongs 228 and 230 of fork 226 include a length L5 of approximately 2.25 mm to approximately 2.35 mm. Anchor device 200 includes an overall length L6 of approximately 8.50 mm to approximately 8.70 mm when post 204 is fully seated within body portion 202. As best shown in FIGS. 8 and 9, post 204 is able to travel axially within central bore 212. When post 204 is fully extended from body portion 202, overall length L6 of anchor device 200 increases to approximately 12.5 mm. As such, post 204 is able to travel axially approximately 4.0 mm with respect to body portion 202.

The "telescoping" piston-like feature of anchor device 200 allow fork 226 to be plunged/translate to the depth of 4 mm via the length of the screwdriver tip driver to allow the suture/suture associated materials to be inserted to the maximal depth of a predrilled hole within bone and affixed into the aforementioned hole via advancing the threading 220 of body portion 202 into the bone. During the advancement of the screw body portion 202, the distance between second end 208 of body portion 202 and a proximal end of fork 226 will decrease (similar to the ascension of a piston). Placement of the suture materials at a maximum depth ensures maximal surface area contact of the suture material within bone further increasing the overall strength of the repair and lessening the chance of repair failure.

Still referring to FIG. 7, fork 226 includes a first prong 228 and a second prong 230 that is spaced from first prong 228. More specifically, fork 226 defines a suture trough or gap 232 between prongs 228 and 230 that is configured as a trough to receive suture material therein. In the exemplary embodiment, fork 226 defines an outer width W7 taken between opposing exterior surfaces 234 of prongs 228 and 230 of approximately 2.50 mm to approximately 3.0 mm. Each prong 228 and 230 also includes an obliquely oriented inner surface 236 such that each prong 228 and 230 tapers in width in a distal direction. More specifically, opposing inner surfaces 236 define an angle α of approximately 14.0 degrees and approximately 14.9 degrees. Furthermore, fork 226 defines an inner width W8 taken between opposing inner surfaces 236 at a proximal end of prongs 228 and 230 of approximately 1.40 mm to approximately 2.00 mm.

The suture and suture associated materials are manually passed through prongs 228 and 230 of fork 226 and can be secured to the driver tool to pull taut, thereby seating the suture in the suture trough 232 and securing anchor device 200 to the driver tool (not pictured). The suture and suture associated materials can pass through the suture trough 232 either with or without a needle attached, depending on the need of the specific operation. Additionally, fork 226 provides the means for easily loading suture/suture associated material onto the distal aspect of anchor device without requiring a special suture threading tool.

In the exemplary embodiment, fork 226 includes a shoulder 238 at the proximal end of each prong 228 and 230. Shoulders 238 are obliquely oriented with respect to second end 208 of body portion 202 such that shoulders 238 form an angle β of approximately 40 degrees with respect to second end 208 to reduce friction of fork 226 rotation. Furthermore, shoulders 238 are rounded to include a radius of approximately 0.25 mm.

FIG. 9 is an enlarged view of a portion of anchor device 200 illustrating the interaction between body portion 202 and post 204. More specifically, FIG. 7 illustrates head 222 positioned within a cavity 240 of central bore 212. In the exemplary embodiment, mesh core 210 includes a thickness T4 at second end 208 and a thickness T5 immediately proximal of second end 208. In the exemplary embodiment, thickness T4 is greater than thickness T5 such that central bore 212 defines cavity 240 to contain head 222.

In the exemplary embodiment, second end 208 of mesh core 210, having thickness T4, defines a diameter D7 of central bore 212 that is less than a diameter D6 of head 222 of post 204. Furthermore, ring 119 includes inner diameter D8 that is less than a diameter D6 of head 222. As such, head 222 is restrained within bore 212 and cannot be removed from body portion 202. Additionally, shoulders 238 of fork 226 contact second end 208 of body portion 202 to prevent excess axial movement of post 204 within central bore 212. More specifically, in one embodiment, a distal surface 241 of second end 208 is oriented at an angle α of approximately 10 degrees to separate body portion 202 from fork 226 to reduce friction of fork 226 rotation.

As shown in FIG. 9, cavity 240 includes a diameter D9 that is larger than diameter D6 of head 222, and diameter D7 of second end 208 is larger than a diameter D10 of shank 224. Additionally, the axial length of cavity 240 is larger than the axial length of head 222. As such, head 222 and shank 224 are able to not only rotate freely in central bore 212, but also allowed axial movement and may be obliquely oriented with respect to body portion 202. The ability to be angled with respect to body portion 202 enables anchor 200 to be secured to the patient's bone at various angles and does not require post 204 to be parallel in orientation with body portion 202. The cylindrical body portion 202 coupled with the built-in clearance (within second end 208 of mesh core 210) that head 222 and shank 224 reside within allows for a 360 degrees unabated polyaxial rotation of fork 226 respective to the body portion 202.

Figure 10:
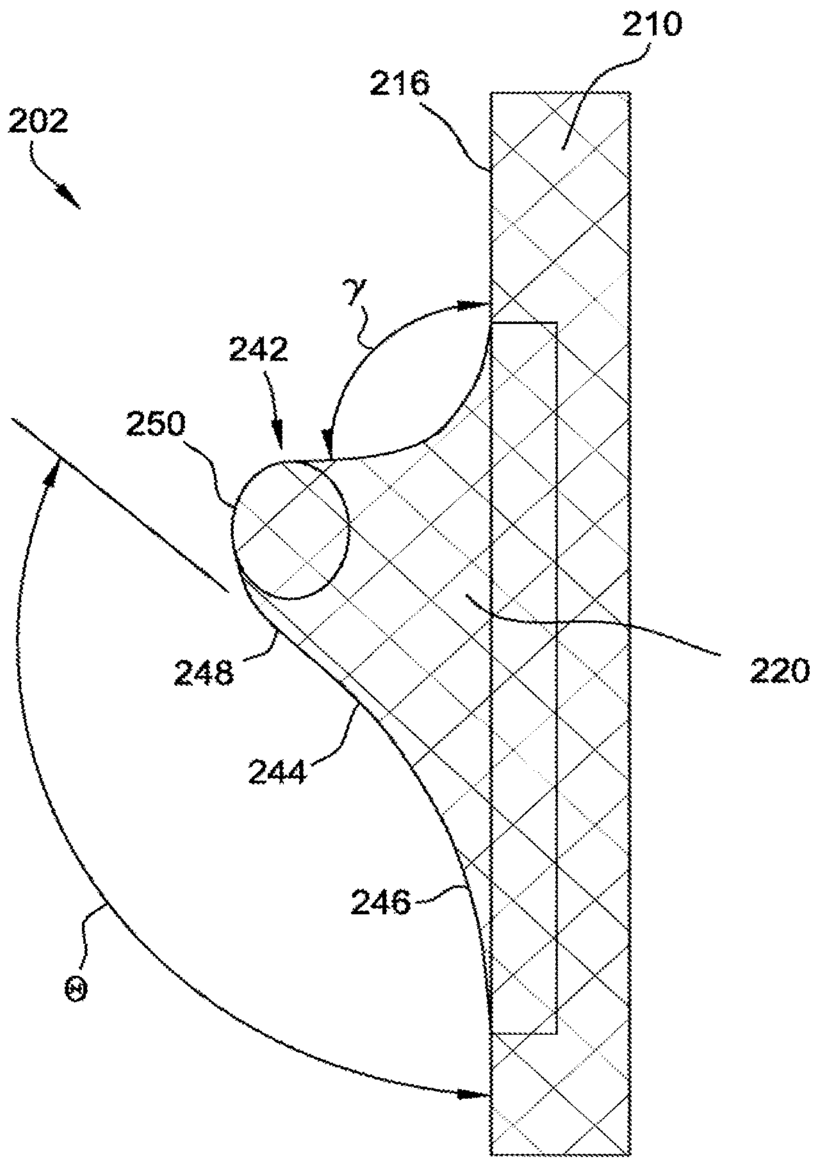
FIG. 10 is an enlarged view of a portion of the trabecular suture anchor shown in FIG. 6 illustrating exemplary threading on a body of the anchor.

FIG. 10 is an enlarged view of body portion 202 illustrating a detailed view of thread 220. In the exemplary embodiment, Thread 220 includes a top surface 242 that is oriented at an angle γ of approximately 93 degrees with respect to exterior surface 216 of mesh core 210 above thread 220. Thread 220 also includes a bottom surface 244 that includes a curved portion 246 extending from exterior surface 216 and a planar portion 248 extending from curved portion 246. In the exemplary embodiment, curved portion 246 defines a radius of approximately 0.8 mm to approximately 1.16 mm, and planar portion 248 is oriented at an angle θ of approximately 125 degrees with respect to exterior surface 216 below thread 220. Furthermore, thread 220 includes an edge 250 that is rounded at a radius of approximately 0.20 mm to approximately 0.25 mm.

In operation, the suture and suture associated materials are manually passed through prongs 228 and 230 of fork 226 and can be secured to the driver tool to pull taut, thereby seating the suture in the suture trough 232 and securing anchor device 200 to the driver tool (not pictured). The drive tool is then inserted into opening 213 and contacts head 222 of post 204 to push suture and/or suture associated materials into a pre-made hole in the patient's bone by fork 226. The drive tool can then rotate to screw anchor device 200 and suture/suture associated materials into the bone. The suture and/or suture associated materials are then adhered/anchored to other tissues as per practitioner preference by stretching the suture/suture associated materials to a separately created hole in the same manner described above. The suture or suture associated materials exit on any side of anchor device 200 post implantation into the bone. Bone ingrowth/osteointegration through mesh core 210 during the healing process further stabilizes anchor device 200 into the bone.

This surgically implanted anchor provides an important technical advantage by providing a means of osteointegration/bone ingrowth throughout the core/body of the implant while in bone. The mesh/porosity of the anchor allows bone to integrate circumferentially through the 3D trabecular mesh body of the implant.

Another advantage is that this implant does not require any threading of suture as it does not contain any eyelet throughout the construct. Furthermore, the 360 degree rotating fork can be stabilized from its dynamic state simply by holding the suture within the tines of the fork with manual tension giving a surgeon control of the entire implant throughout the implantation process.

The design of this implant provides a clinical advantage by eliminating or greatly reducing mechanical failure of the anchor due to the osteointegration thus eliminating reducing hardware disengagement.

In summary, the present embodiment describes 3D-Printed Osteointegrating Trabecular Metal Bone Anchors with affixed fork suture trough for use in attaching tissue to bone. The anchor includes a solid threaded bone anchor around a trabecular mesh core body having a major diameter, a minor diameter, a drive head, and a distally located freely articulating fork. A suture trough is formed between the tines of the fork having a width greater than or equal to the diameter of the suture and suture associated materials and a depth below the minor diameter greater than or equal to the diameter of the suture and suture associated materials. The suture seats within the suture trough of the fork during insertion of the bone anchor into the bone. The present embodiment allows needles to be attached to the suture and suture associated materials prior to insertion of the bone anchor into the bone, allows for osteointegration/bone ingrowth lessening the potential for the implant to dislodge, and an all-in-one piece design eliminating a surgeon concerns that a separate fork will separate from the anchor driver prior to implantation.

Although the present disclosure, anchor device, has been described in detail, it should be understood that various changes, alterations, and substitutions can be made hereto without deviating from the intention and scope of the disclosure as described by the appended claims.

Although specific features of various implementations of the disclosure may be shown in some drawings and not in others, this is for convenience only. In accordance with the principles of the disclosure, any feature of a drawing may be referenced and/or claimed in combination with any feature of any other drawing.

This written description uses examples to disclose various implementations, which include the best mode, to enable any person skilled in the art to practice those implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An anchor device configured to attach a suture material to bone, the anchor device comprising:

- a body portion having a first end and a second end, a body portion longitudinal axis extending through the first end and the second end, the body portion comprising:
  - a trabecular mesh core that at least partially defines a central bore, the central bore comprising a cavity closer to the second end than to the first end of the body portion, the cavity having a first diameter, a first portion of the central bore on a first end of the cavity having a second diameter, a second portion of the central bore on a second end of the cavity having a third diameter, the first diameter being greater than the second diameter and the third diameter; and
  - at least one thread extending along an exterior of the trabecular mesh core; and
- a post comprising a head, a shank, and a fork along a post longitudinal axis, the shank connecting the head to the fork, the head having a fourth diameter and the shank having a fifth diameter, the fourth diameter being smaller than the first diameter but greater than the second diameter and the third diameter, the fifth diameter being smaller than the third diameter and the fourth diameter, the head being retained within the cavity and the fork extending from the second end of the body portion, the head being rotatable within the cavity to rotate the post longitudinal axis to be at an angle with respect to the body portion longitudinal axis.

2. The anchor device of claim 1, wherein an axial length of the cavity is greater than an axial length of the head.

3. The anchor device of claim 2, wherein the head is allowed restricted axial movements within the cavity.

4. The anchor device of claim 3, wherein shoulders of the fork are configured to contact the second end of the body portion to prevent excess axial movements of the head within the central bore.

5. The anchor device of claim 1, wherein a distal surface of the second end of the body portion is angled relative to shoulder of the fork.

6. The anchor device of claim 1, wherein the angle is an oblique angle.

7. The anchor device of claim 1, wherein the post is configured to rotate freely with respect to the body portion.

8. The anchor device of claim 1, wherein the head is not removable from the body portion.

9. An anchor device configured to attach a suture material to bone, the anchor device comprising:

a body portion having a first end and a second end, the body portion comprising:

a trabecular mesh core that at least partially defines a central bore, the central bore comprising a cavity closer to the second end than to the first end of the body portion, the central bore terminating at a neck at the second end adjacent the cavity, the neck having a smaller inner diameter than the cavity; and at least one thread extending along an exterior of the trabecular mesh core; and a post comprising a head, a shank, and a fork, the shank connecting the head to the fork, the head positioned within the cavity, the shank positioned within the neck, and the fork extending from the second end of the body portion, the head being rotatable within the cavity relative to the body portion to orient the post at an angle with respect to the body portion.

10. The anchor device of claim 9, wherein an axial length of the cavity is greater than an axial length of the head.

11. The anchor device of claim 10, wherein the cavity has a first diameter, a portion of the central bore on an opposite end of the cavity from the neck has a second diameter, and the neck has a third diameter, the first diameter being greater than the second diameter and the third diameter so as to retain the head within the cavity.

12. The anchor device of claim 11, wherein the head is freely rotatable and allowed restricted axial movements within the cavity.

13. The anchor device of claim 11, wherein shoulders of the fork are configured to contact the second end of the body portion to prevent excess axial movements of the head within the central bore.

14. The anchor device of claim 11, wherein the head has a fourth diameter and the shank has a fifth diameter, the fourth diameter being smaller than the first diameter but greater than the second diameter and the third diameter, the fifth diameter being smaller than the third diameter.

15. The anchor device of claim 9, wherein a distal surface of the second end of the body portion is angled relative to shoulder of the fork.

16. The anchor device of claim 9, wherein the head is not removable from the body portion.

17. The anchor device of claim 9, wherein the angle is an oblique angle.

* * * * *